United States Patent [19]

Imashiro et al.

[11] Patent Number: 5,360,933

[45] Date of Patent: Nov. 1, 1994

[54] TETRAMETHYLXYLYLENE CARBODIIMIDE

[75] Inventors: Yasuo Imashiro; Ikuo Takahashi, both of Tokyo, Japan

[73] Assignee: Nisshinbo Industries, Inc., Tokyo, Japan

[21] Appl. No.: 992,029

[22] Filed: Dec. 17, 1992

[30] Foreign Application Priority Data

Dec. 26, 1991 [JP] Japan ................... 3-359449

[51] Int. Cl.$^5$ ................. C08G 18/70; C07C 267/00
[52] U.S. Cl. ....................... 564/252; 528/67
[58] Field of Search ................. 564/252; 528/67

[56] References Cited

U.S. PATENT DOCUMENTS

| | | | |
|---|---|---|---|
| 4,072,712 | 2/1978 | Meisert et al. | 260/566 R |
| 4,419,294 | 12/1983 | Feldman et al. | 260/453 A |
| 5,198,522 | 3/1993 | Steppan et al. | 528/67 |

FOREIGN PATENT DOCUMENTS 0120305 10/1984 European Pat. Off.

*Primary Examiner*—Peter O'Sullivan
*Attorney, Agent, or Firm*—Adduci, Mastriani Schaumberg & Schill

[57] ABSTRACT

The present invention provides a tetramethylxylylene carbodiimide represented by the following formula

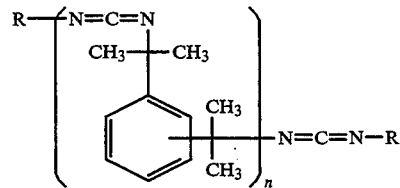

wherein R is a monoisocyanate residue and n represents an integer of 1 or more.

Said carbodiimide has good storage stability owing to reduced reactivity and gives good handleability in a reaction with an active hydrogen compound.

12 Claims, No Drawings

TETRAMETHYLXYLYLENE CARBODIIMIDE

BACKGROUND OF THE INVENTION (1) Field of the Invention

The present invention relates to a novel carbodiimide. More particularly, the present invention relates to a carbodiimide which has good storage stability owing to the reduced reactivity and which gives good handleability in the reaction with an active hydrogen compound.

(2) Description of the Prior Art

Polycarbodiimides are known to have high heat resistance and are in use as a thermosetting resin, for example, as a molding material by subjecting a powdery polycarbodiimide to hot pressing or the like.

Of the polycarbodiimides, aromatic polycarbodiimides had been used mainly. Recently, however, the production and application of aliphatic polycarbodiimide were reported. For example, Japanese Patent Application Kokai (Laid-Open) No. 187029/1984 discloses a polycarbodiimide derived from isophorone diisocyanate and a method for cross-linking a resin for aqueous coating, using said polycarbodiimide.

The above cross-linking of a resin for aqueous coating refers to a reaction between the carbodiimide group of a polycarbodiimide and the active hydrogen of an active hydrogen compound, for example, a reaction between a carbodiimide group and a carboxylic acid residue contained in an aqueous acrylic resin.

Conventionally known aliphatic polycarbodiimides, for example, polycarbodiimides derived from isophorone diisocyanate, however, have had the following problem. That is, the reaction between an aliphatic polycarbodiimide and an active hydrogen compound proceeds after addition of a cross-linking resin to a coating resin, even when the reaction is carried out under low temperature, resulting in poor storage stability and shortened usable time as a coating.

The conventionally known aliphatic polycarbodiimides have also had the following problem. That is, when mixed with an active hydrogen compound, they immediately react with the compound due to their high reactivity, giving rise to precipitation or gelling and making difficult the handling of the reaction mixture.

The present invention has been made in order to provide a carbodiimide which is free from the above problems of the prior art, which has good storage stability and which gives good handleability in the reaction with an active hydrogen compound.

SUMMARY OF THE INVENTION

According to the present invention there is provided a tetramethylxylylene carbodiimide represented by the following formula

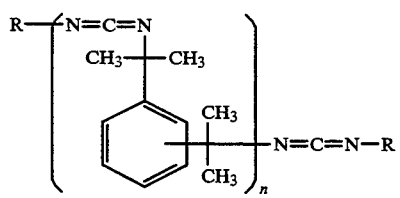

wherein R represents the residue of a monoisocyanate and n represents an integer of 1 or more.

DETAILED DESCRIPTION OF THE INVENTION

The present invention is hereinafter described in detail.

The carbodiimide of the present invention is represented by the above formula and is synthesized from, for example, m-tetramethylxylylene diisocyanate of the following formula

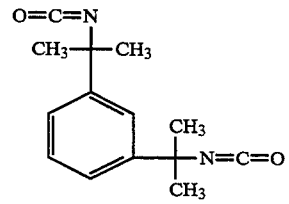

or p-tetramethylxylylene diisocyanate of the following formula

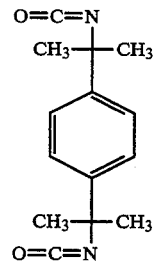

In the above formula for the present carbodiimide, n represents an integer of 1 or more and refers to the polymerization degree of said carbodiimide. As is easily understood from the formula, the carbodiimide of the present invention has structural isomerism, and there are structural isomers in the present carbodiimide.

The carbodiimide of the present invention having the above feature can be produced by a condensation reaction between tetramethylxylylene diisocyanate and a monoisocyanate, in which the removal of carbon dioxide takes place. It can be basically produced according to the conventional processes for producing a polycarbodiimide described in, for example, U.S. Pat. No. 2,941,956; Japanese Patent Publication No. 33279/1972; J. Org. Chem., 28, 2069–2075 (1963); Chemical Review 1981, Vol. 81, Nov. 4, pp. 619–621.

As the monoisocyanate, there can be used, for example, n-butyl isocyanate, tert-butyl isocyanate, isobutyl isocyanate, ethyl isocyanate, n-propyl isocyanate, isopropyl isocyanate, cyclohexyl isocyanate and n-octadecyl isocyanate. Of these, n-butyl isocyanate is particularly preferable. The amount ratio of monoisocyanate and diisocyanate can be, for example, 2:1 to 2:30. In this case, n is 1 to 30.

In the present invention, when no mono isocyanate is used, the reaction time is very long and it is difficult to conduct the reaction until no isocyanate remains.

As the preferable solvent used in the present invention, there can be mentioned, for example, aliphatic acetate type solvents such as amyl acetate, propyleneglycol monomethylether acetate, diethyleneglycol monoethylether acetate, cellosolve acetate, butyl acetate, hexyleneglycol diacetate and the like.

The condensation reaction between tetramethylxylylene diisocyanate and a monoisocyanate, in which the removal of carbon dioxide takes place, proceeds in the presence of a carbodiimidization catalyst. As said catalyst, there can be used, for example, phospholene oxides such as 1-phenyl-2-phospholene-1-oxide, 3-methyl-2-phospholene-1-oxide, 1-ethyl-3-methyl-2-phospholene-1-oxide, 1-ethyl-2-phospholene-1oxide, 3-methyl-1-phenyl-2-phospholene-1-oxide, 3-phospholene isomers thereof and the like. 3-Methyl-1-phenyl-2-phospholene-1-oxide is preferable in view of the catalytic activity.

The temperature of the condensation reaction is preferably about 80°–180° C. When the temperature is lower than the above range, the reaction time is very long. When the temperature is higher than the above range, side reactions take place and it is impossible to obtain a solution of a carbodiimide of good quality. The total concentration of tetramethylxylylene diisocyanate and a monoisocyanate is preferably about 80% by weight or less. When the monomer concentration is more than the above upper limit, the viscosity of the reaction system is too high and the reaction time is too long.

The reaction between tetramethylxylylene diisocyanate and a monoisocyanate is conducted in a current of an inert gas such as nitrogen or the like, in order to complete the reaction quickly.

Next, the present invention is described in more detail by way of Examples.

EXAMPLE 1

732 g of m-tetramethylxylylene diisocyanate and 199 g of butyl isocyanate were reacted in the presence of 9.30 g of a carbodiimidization catalyst (3-methyl-1-phenyl-2-phospholene-1-oxide) in 756 g of propyleneglycol monomethylether acetate (resin concentration=50% by weight) at 150° C. for 91 hours to obtain a solution of a polycarbodiimide having a polymerization degree of 3. The solution was stable in a constant temperature chamber of 70° C. for more than 1 month and gave excellent storage stability.

EXAMPLE 2

732 g of m-tetramethylxylylene diisocyanate and 66 g of butyl isocyanate were reacted in the presence of 7.98 g of a carbodiimidization catalyst (3-methyl-1-phenyl-2-phospholene-1-oxide) 651 g of propyleneglycol monomethylether acetate (resin concentration=50% by weight) at 150° C. for 240 hours to obtain a solution of a polycarbodiimide having a polymerization degree of 9. The solution was stable in a constant temperature chamber of 70° C. for more than 1 month and gave excellent storage stability.

EXAMPLE 3

585 g of m-tetramethylxylylene diisocyanate and 24.9 g of butyl isocyanate were reacted in the presence of 12.18 g of a carbodiimidization catalyst (3-methyl-1-phenyl-2-phospholene-1-oxide) in 1996 g of propyleneglycol monomethylether acetate ( resin concentration=20% by weight) at 150° C. for 326 hours to obtain a solution of a polycarbodiimide having a polymerization degree of 19. The solution was concentrated to a 50% by weight concentration, and the concentrated solution was stable in a constant temperature chamber of 70° C. for more than 1 month and gave excellent storage stability.

EXAMPLE 4

585 g of m-tetramethylxylylene diisocyanate and 24.0 g of butyl isocyanate were reacted in the presence of 12.18 g of a carbodiimidization catalyst (3-methyl-1-phenyl-2-phospholene-1-oxide) in 1497 g of propyleneglycol monomethylether acetate (resin concentration=25% by weight) at 150° C. for 348 hours to obtain a solution of a polycarbodiimide having a polymerization degree of 19. The solution was concentrated to a 50% by weight concentration, and the concentrated solution was stable in a constant temperature chamber of 70° C. for more than 1 month and gave excellent storage stability.

EXAMPLE 5

244 g of m-tetramethylxylylene diisocyanate and 66.3 g of butyl isocyanate were reacted in the presence of 3.1 g of a carbodiimidization catalyst (3-methyl-1-phenyl-2-phospholene-1-oxide) in 252 g of amyl acetate (resin concentration=50% by weight) at 140° C. for 67 hours to obtain a solution of a polycarbodiimide having a polymerization degree of 3. The solution was stable in a constant temperature chamber of 70° C. for more than 1 month and gave excellent storage stability.

EXAMPLE 6

183 g of m-tetramethylxylylene diisocyanate and 16.5 g of butyl isocyanate were reacted in the presence of 4.0 g of a carbodiimidization catalyst (3-methyl-1-phenyl-2-phospholene-1oxide) in 163 g of diethyleneglycol monoethylether acetate (resin concentration=50% by weight) at 160° C. for 81 hours to obtain a solution of a polycarbodiimide having a polymerization degree of 9. The solution was stable in a constant temperature chamber of 70° C. for more than 1 month and gave excellent storage stability.

Comparative Example 1

210.9 g of isophorone diisocyanate and 9.9 g of butyl isocyanate were reacted in the presence of a carbodiimidization catalyst (3-methyl-1-phenyl-2-phospholene-1-oxide) in 530.4 g of propyleneglycol monomethylether acetate (resin concentration=25% by weight) at 150° C. for 69 hours to obtain a solution of a polycarbodiimide having a polymerization degree of 19. The solution was concentrated to a 50% by weight concentration, and the concentrated solution gave gelling in 144 hours when stored in a constant temperature chamber of 70° C.

REFERENCE EXAMPLES

[Reaction between polycarbodiimide and benzoic acid]

Reference Example 1

0.5 g of the polycarbodiimide solution obtained in Example 1 was mixed with 20 g of a propyleneglycol monomethylether acetate solution containing 10% of benzoic acid. The mixture was allowed to stand at room temperature. Analysis by IR absorption spectrometry indicated that the absorption of polycarbodiimide group disappeared in 4 hours and the reaction between carbodiimide group and carboxyl group was over.

Reference Example 2

0.5 g of the polycarbodiimide solution obtained in Example 1 was mixed with 20 g of a propyleneglycol monomethylether acetate solution containing 10% of benzoic acid. The mixture was allowed to stand in a constant temperature chamber of 50° C. Analysis by IR absorption spectrometry indicated that the absorption of carbodiimide group disappeared in 2 hours and the reaction between carbodiimide group and carboxyl group was over.

Reference Example 3

0.5 g of the polycarbodiimide solution obtained in Example 2 was mixed with 20 g of a propyleneglycol monomethylether acetate solution containing 10% of benzoic acid. The mixture was allowed to stand at room temperature. Analysis by IR absorption spectrometry indicated that the absorption of polycarbodiimide group disappeared in 6 hours and the reaction between carbodiimide group and carboxyl group was over.

Reference Example 4

0.5 g of the polycarbodiimide solution obtained in Example 2 was mixed with 20 g of a propyleneglycol monomethylether acetate solution containing 10% of benzoic acid. The mixture was allowed to stand in a constant temperature chamber of 50° C. Analysis by IR absorption spectrometry indicated that the absorption of carbodiimide group disappeared in 5 hours and the reaction between carbodiimide group and carboxyl group was over.

Reference Example 5

0.5 g of the concentrated solution containing 50% by weight of a polycarbodiimide, obtained in Example 4 was mixed with 20 g of a propyleneglycol monomethylether acetate solution containing 10% of benzoic acid. The mixture was allowed to stand at room temperature. Analysis by IR absorption spectrometry indicated that the absorption of carbodiimide group disappeared in 9 hours and the reaction between carbodiimide group and carboxyl group was over.

Reference Example 6

0.5 g of the concentrated solution containing 50% by weight of a polycarbodiimide, obtained in Comparative Example 1 was mixed with 20 g of a propyleneglycol monomethylether acetate containing 10% of benzoic acid. The mixture gave rise to a reaction momentarily and became cloudy. Analysis by IR spectrometry indicated that the cloudy mixture showed no absorption of carbodiimide group.

[Reaction between polycarbodiimide and styrene-acrylic resin]

Reference Example 7

23.8 g of the polycarbodiimide solution obtained in Example 1 was mixed with 10 g Of a styrene-acrylic resin emulsion (acid value=300, resin concentration=30% by weight) and the mixture was allowed to stand at room temperature. Analysis by IR absorption spectrometry indicated that the absorption of carbodiimide group disappeared in 3 hours and the reaction mixture was stiffened.

Reference Example 8

23.8 g of the polycarbodiimide solution obtained in Example 1 was mixed with 10 g of a styrene-acrylic resin emulsion (acid value=300, resin concentration=30% by weight) and the mixture was allowed to stand in the constant temperature chamber of 50° C. Analysis by IR absorption spectrometry indicated that the absorption of carbodiimide group disappeared in 1 hour and the reaction mixture was stiffened.

Reference Example 9

10 g of a styrene-acrylic resin emulsion (acid value=300, resin concentration=30% by weight) was allowed to stand in a constant temperature chamber of 50° C. for 24 hours. IR absorption spectrometry remained unchanged and the reaction mixture was not stiffened.

As described above, the polytetramethylxylylene carbodiimide is very stable; therefore, even after being added to an active hydrogen compound at room temperature, is stable over a long period of time and is easy to handle.

What is claimed is:

1. A tetramethylxylylene carbodiimide of the formula

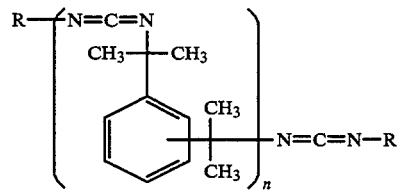

where R is the residue of a monoisocyanate and n is an integer of 1 or more.

2. A tetramethylxylylene carbodiimide of claim 1 of the formula

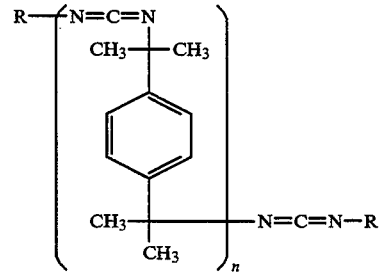

3. A tetramethylxylylene carbodiimide of claim 1 of the formula

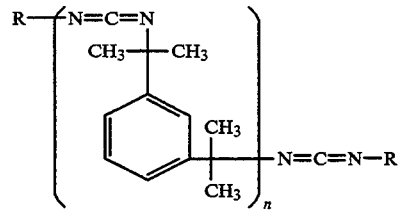

4. A tetramethylxylylene carbodiimide of claim 1 where n is an integer of 1 to 30.

5. A tetramethylxylylene carbodiimide of claim 2 where n is an integer of 1 to 30.

6. A tetramethylxylylene carbodiimide of claim 3 where n is an integer of 1 to 30.

7. A tetramethylxylylene carbodiimide of claim 1 where R is an alkyl group of up to 18 carbon atoms.

8. A tetramethylxylylene carbodiimide of claim 2 where R is an alkyl group of up to 18 carbon atoms.

9. A tetramethylxylylene carbodiimide of claim 3 where R is an alkyl group of up to 18 carbon atoms.

10. A tetramethylxylylene carbodiimide of claim 4 where R is an alkyl group of up to 18 carbon atoms.

11. A tetramethylxylylene carbodiimide of claim 5 where R is an alkyl group of up to 18 carbon atoms.

12. A tetramethylxylylene carbodiimide of claim 6 where R is an alkyl group of up to 18 carbon atoms.

* * * * *